United States Patent
Koizumi et al.

(10) Patent No.: US 6,946,281 B2
(45) Date of Patent: Sep. 20, 2005

(54) N-ACETYLGLUCOSAMINE 2-EPIMERASE AND DNA ENCODING THE SAME

(75) Inventors: Satoshi Koizumi, Yokohama (JP); Kazuhiko Tabata, Hofu (JP); Tetsuo Endo, Tokyo (JP); Akio Ozaki, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 96 days.

(21) Appl. No.: 10/378,745

(22) Filed: Mar. 4, 2003

(65) Prior Publication Data

US 2003/0157659 A1 Aug. 21, 2003

Related U.S. Application Data

(63) Continuation of application No. 09/890,912, filed as application No. PCT/JP00/00702 on Feb. 9, 2000, now abandoned.

(30) Foreign Application Priority Data

Feb. 9, 1999 (JP) ............................................. 11-31035

(51) Int. Cl.$^7$ .......................... C12N 9/90; C12N 15/61; C12N 19/24
(52) U.S. Cl. .................... 435/233; 435/252.33; 435/94; 435/320.1; 536/23.2
(58) Field of Search ........................... 435/233, 252.33, 435/94, 326.1; 536/23.2

(56) References Cited

FOREIGN PATENT DOCUMENTS

EP    0 708 177    4/1996

OTHER PUBLICATIONS

Kaneko, et al., "Sequence Analysis of the Genome of the Unicellular . . . ", DNA Research, vol. 3 (1996), pp. 109–136.
Maru, et al., "Molecular Cloning and Identification of N–Acyl–D–glucosamine . . . ", The Journal of Biochemical Chemistry, vol. 271, No. 27 (1996), pp. 16294–16299.
Takahashi, et al., "Human Renin–Binding Protein Is the Enzyme . . . ", J. Biochem., vol. 125 (1999), pp. 348–353.
Maru, et al., "Simple and Large–scale production of N–acetylneuraminic . . . ", Carbohydrate Research, vol. 306 (1998), pp. 575–578.
Nakamura, et al., "CyanoBase, a www database containing . . . ", Nucleic Acids Research, 1998, vol. 26 No. 1 (1998), pp. 63–67.
Kaneko, et al., (1996) Accession No. P74124.

*Primary Examiner*—Charles L. Patterson, Jr.
(74) *Attorney, Agent, or Firm*—Fitzpatrick, Cella, Harper & Scinto

(57) ABSTRACT

The present invention provides a novel protein having N-acetylglucosamine 2-epimerase activity; a DNA encoding the protein; a recombinant vector containing the DNA; a transformant obtainable by introducing the recombinant vector into a host cell; and a process for producing the protein or N-acetylmannosamine using the transformant.

11 Claims, 1 Drawing Sheet

N-ACETYLGLUCOSAMINE 2-EPIMERASE AND DNA ENCODING THE SAME

This application is a continuation of application Ser. No. 09/890,912 filed Aug. 8, 2001 now abandoned which in turn is a national phase of PCT application No. PCT/JP00/00702 filed Feb. 9, 2000.

FIELD OF THE INVENTION

The present invention relates to a protein having N-acetylglucosamine 2-epimerase activity, a DNA encoding the protein, a recombinant DNA containing the DNA, a transformant carring the recombinant DNA, a process for producing N-acetylglucosamine 2-epimerase using the transformant, and a process for producing N-acetylmannosamine using the transformant. N-Acetylmannosamine is an important compound as an intermediate for the biosynthesis of N-acetylneuraminic acid.

BACKGROUND ART

N-acetylglucosamine 2-epimerase is known to be present in swine and rats, and properties of the enzyme derived from swine have been examined (*Biochemistry*, 17: 3363 (1970)). Furthermore, the gene derived from swine has been isolated (*J. Biol. Chem.*, 271: 16294 (1996)). However, the activity of the enzyme derived from microorganisms has not been known.

In *Synechocystis* sp. (PCC 6803) which is one of Cyanobacteria, full nucleotide sequence of the genome has been determined (*DNA Research*, 3: 109 (1996), *Nucleic Acids Research*, 26: 63 (1998)), but the N-acetylglucosamine 2-epimerase gene has not been identified.

DISCLOSURE OF THE INVENTION

The object of the present invention is to provide a protein having N-acetylglucosamine 2-epimerase activity, a DNA encoding the protein, a process for producing a protein having N-acetylglucosamine 2-epimerase activity using the DNA, and a process for producing N-acetylmannosamine using the protein.

In order to attain the above object, the present inventors have conducted intensive studies to search for a sequence having homology with the amino acid sequence of N-acetylglucosamine 2-epimerase derived from swine based on the sequence information on *Synechocystis* sp. (PCC 6803) in which full nucleotide sequence of its genomic DNA has been determined. As a result of the studies, the present inventors have first found and isolated, from a microorganism, a novel DNA encoding N-acetylglucosamine 2-epimerase, which has not been identified so far, and the present invention has been accomplished.

Specifically, the present invention relates to the following subject matters (1) to (10):

(1) A protein selected from the following proteins (a) and (b):

(a) a protein comprising the amino acid sequence represented by SEQ ID NO:1, and
(b) a protein comprising an amino acid sequence wherein at least one amino acid is deleted, replaced or added in the amino acid sequence of the protein (a), and having N-acetylglucosamine 2-epimerase activity.

The above-mentioned protein comprising an amino acid sequence wherein at least one amino acids is deleted, replaced or added in the amino acid sequence of the protein (a) and having N-acetylglucosamine 2-epimerase activity can be obtained by site-directed mutagenesis described in, for example, *Molecular Cloning, A Laboratory Manual*, 2nd ed., Cold Spring Harbor Laboratory Press (1989) (hereinafter referred to as "*Molecular Cloning*, 2nd ed."), *Current Protocols in Molecular Biology*, John Wiley & Sons (1987–1997) (hereinafter referred to as "*Current Protocols in Molecular Biology*"), *Nucleic Acids Research*, 10: 6487 (1982), *Proc. Natl. Acad. Sci. USA*, 79: 6409 (1982), *Gene*, 34: 315 (1985), *Nuc. Acids. Res.*, 13: 4431 (1985), *Proc. Natl. Acad Sci. USA*, 82: 488 (1985) and the like. For example, the protein can be obtained by introducing site-directed mutagenesis into DNA encoding a protein having the amino acid sequence represented by SEQ ID NO:1.

The number of amino acids which are deleted, replaced or added is not particularly limited; however, it is such a number that the deletion, replacement or addition can be carried out according to a known method, e.g. the above site-directed mutagenesis and the like, and the number is usually one to several decades, preferably one to 20, more preferably one to 10, and most preferably one to 5, amino acids.

(2) A DNA encoding the protein according to (1).
(3) A DNA selected from the following DNAs (a) and (b):

(a) a DNA comprising the nucleotide sequence represented by SEQ ID NO:2, and
(b) a DNA which hybridizes with the DNA (a) under the stringent conditions and which encodes a protein having N-acetylglucosamine 2-epimerase activity.

The recitation "DNA which hybridizes with the DNA under the stringent conditions" as used herein refer to a DNA obtained by colony hybridization, plaque hybridization, Southern hybridization or the like using, as a probe, the DNA comprising the nucleotide sequence represented by SEQ ID NO:2. The DNA includes, for example, a DNA which can be identified by carrying out hybridization at 65° C. in the presence of 0.7–1.0 M NaCl using a filter on which a DNA prepared from colonies or plaques is immobilized, and then washing the filter with 0.1 to 2-fold concentrated SSC solution (1-fold concentrated SSC is composed of 150 mM sodium chloride and 15 mM sodium citrate) at 65° C.

The hybridization can be carried out in accordance with a known method described in, for example, *Molecular Cloning*, 2nd ed., *Current Protocols in Molecular Biology*, *DNA Cloning 1: Core Techniques, A Practical Approach*, 2nd ed., Oxford University (1995) or the like. Specific examples of the DNA which can be hybridized include a DNA having homology of 80% or more, preferably 95% or more, with the nucleotide sequence represented by SEQ ID NO:2 when calculated using BLAST (*J. Mol. Biol.*, 215: 403 (1990)), FASTA (*Methods in Enzymology*, 183: 63–98 (1990)), or the like.

(4) The DNA according to (2) or (3), wherein the DNA is a DNA derived from a microorganism belonging to Cyanobacteria.
(5) The DNA according to any one of (2) to (4), wherein the DNA derived from a microorganism belonging to Cyanobacteria is a DNA derived from a microorganism belonging to the genus *Synechocystis*.
(6) A recombinant DNA obtainable by inserting a DNA selected from the DNAs according to any one of (2) to (5) into a vector.

(7) A transformant obtainable by introducing the recombinant DNA according to (6) into a host cell.
(8) The transformant according to (7), wherein the transformant is *Escherichia coli*.
(9) A process for producing a protein having N-acetylglucosamine 2-epimerase activity, which comprises culturing the transformant according to (7) or (8) in a medium to produce and accumulate the protein having N-acetylglucosamine 2-epimerase activity in the culture; and recovering the protein from the culture.
(10) A process for producing N-acetylmannosamine, which comprises selecting, as an enzyme source, a culture of the transformant according to (7) or (8) or a treated product of the culture; allowing the enzyme source and N-acetylglucosamine to be present in an aqueous medium to produce and accumulate N-acetylmannosamine in the aqueous medium; and recovering N-acetylmannosamine from the aqueous medium.

The present invention is explained below in detail.
<1> Preparation of the DNA of the Present Invention
(1) Identification of the Gene on Data Base Since the nucleotide sequence of the genomic DNA of *Synechocystis* sp. (PCC 6803) has been fully determined (*DNA Research*, 3: 109 (1996); *Nucleic Acids Research*, 26: 63 (1998)), a homology search can be carried out with the data base such as CyanoBase (http://www.kazusa.or.jp/cyano/) and the like.

As the Query to be used in the homology search, any sequence of N-acetylglucosamine 2-epimerase can be used. Examples include the amino acid sequence of N-acetylglucosamine 2-epimerase derived from swine (*J. Biol. Chem.*, 271: 16294 (1996)).

The searching may be carried out by any of known method, so long as it can be used, and a homology search based on GenBank or CyanoBase can be exemplified.
(2) Preparation of the DNA of the Present Invention The DNA of the present invention is desirably prepared from a microorganism belonging to Cyanobacteria. Examples of the microorganism belonging to Cyanobacteria include the genus *Synechocystis*, such as *Synechocystis* sp. PCC 6803 and the like.

A microorganism belonging to Cyanobacteria is cultured by a known method (for example, *J. Gen. Microbiol.*, 111: 1 (1979)).

After culturing, chromosomal DNA of the microorganism is isolated and purified by a known method (for example, *Current Protocols in Molecular Biology*, John Wiley & Sons (1987–1997)).

A fragment containing the DNA of the present invention can be obtained by preparing a primer based on the nucleotide sequence of the genomic DNA identified in the above (1), and carrying out PCR (*PCR Protocols*, Academic Press (1990)) using the genomic DNA as a template.

The desired DNA can be obtained by hybridization using, as a probe, a synthetic DNA designed based on the nucleotide sequence of the genomic DNA.

The nucleotide sequence of the DNA obtained can be determined by inserting the DNA, directly or after digestion with a suitable restriction enzyme or the like, into a vector and analyzing it by a generally-used nucleotide sequence analyzing method such as the dideoxy method (*Proc. Natl. Acad. Sci. USA*, 74: 5463 (1997)) or using an apparatus for nucleotide sequence analysis such as 373A DNA sequencer (manufactured by Perkin Elmer) or the like.

The vector in which the DNA is inserted includes pBluescript KS(+) (manufactured by Stratagene), pDIRECT (*Nucleic Acids Research*, 18: 6069 (1990)), pCR-Script Amp SK(+) (manufactured by Stratagene), pT7Blue (manufactured by Novagene), pCRII (manufactured by Invitrogen), pCR-TRAP manufactured by Gene Hunter), pNoTAT7 (manufactured by 5 Prime→3 Prime) and the like.

Examples of the DNA comprising a novel nucleotide sequence obtained by the above method include DNA comprising the sequence represented by SEQ ID NO:2 and the like.

Examples of *Escherichia coli* containing a plasmid containing the DNA comprising the sequence represented by SEQ ID NO:2 include *Escherichia coli* NM522/pYP16.

Furthermore, the desired DNA can also be prepared by chemical synthesis based on the nucleotide sequence information obtained above using a DNA synthesizer, such as a DNA synthesizer 8905 Type manufactured Perceptive Biosystems or the like.

Examples of *Escherichia coli* include *Escherichia coli* XL1-Blue, *Escherichia coli* XL2-Blue, *Escherichla coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522 and the like.

Introduction of the recombinant DNA can be carried out by any of the methods for introducing DNA into the above host cell, for example, the method using calcium ion (*Pros. Natl. Acad. Sci. USA*, 69: 2110 (1972)), the protoplast method (Japanese Published Unexamined Patent Application No. 248394/88), electroporation (*Nucleic Acids Research*, 16: 6127 (1988)) and the like.
<2> Preparation of the Protein of the Present Invention The protein of the present invention can be produced by expressing the DNA of the present invention obtained by the method described in (1) in a host cell, for example, as shown below, using a method described in *Molecular Cloning*, 2nd ed., *Current Protocols in Molecular Biology* or the like.

Based on the DNA of the present invention, a DNA fragment of a suitable length containing a region which encodes the protein of the present invention can be prepared, if necessary. Further, DNA useful for improving the production efficiency of the protein of the present invention can be prepared by substituting nucleotides in the nucleotide sequence of the region encoding the protein of the present invention so that it has the most suitable codons for the expression in the host.

The DNA fragment is inserted downstream of a promoter region in a suitable expression vector to construct a recombinant vector.

The recombinant vector is introduced into a host cell suitable for the expression vector to obtain a transformant which produces the protein of the present invention.

Any of bacteria, yeasts, animal cells, insect cells, plant cells, and the like can be used as the host cell so long as it can express the gene of interest.

Examples of the expression vector include those which can replicate autonomously in the above-described host cell or can be integrated into chromosome and have a promoter at such a position that the DNA of the present invention can be transcribed.

When a procaryote cell, such as a bacterium or the like, is used as the host cell, it is preferred that the vector expressing the protein gene of the present invention can replicate autonomously in the bacterium. It is also preferred that the recombinant vector contains a promoter, a ribosome binding sequence, the DNA of the present invention and a transcription termination sequence. A gene regulating the promoter may also be desirably contained.

Examples of the expression vector include pBTrp2, pBTac1 and pBTac2 (all manufactured by Boehringer Mannheim), pKK233-2 (manufactured by Pharmacia), pGEX (manufactured by Pharmacia), pSE280 (manufactured by Invitrogen), pGEMEX-1 (manufactured by Promega), pQE-8 (manufactured by QIAGEN), pET-3 (manufactured by Novagene), pKYP10 (Japanese Published Unexamined Patent Application No. 110600/83), pKYP200 (*Agric. Biol. Chem.*, 48: 669 (1984)), pLSA1 (*Agric. Biol. Chem.*, 53: 277 (1989)), pGEL1 (*Proc. Natl. Acad. Sci. USA*, 82: 4306 (1985)), pBluescript II SK+ (manufactured by Stratagene), pBluescript II SK(−) (manufactured by Stratagene), pTrS30 (prepared from *Escherichia coli* JM109/pTrS30 (FERM BP-5407)), pTrs32 (prepared from *Escherichia coli* JM109/pTrS32 (FERM BP-5408)), pUC19 (*Gene*, 33: 103 (1985)), pSTV28 (manufactured by Takara Shuzo), pUC118 (manufactured by Takara Shuzo), pPA1 (Japanese Published Unexamined Patent Application No. 233798/88), pPAC31 (WO 98/12343) and the like.

Any promoter can be used so long as it can function in the host cell such as *Escherichia coli* or the like. Examples include promoters derived from *Escherichia coli*, phage and the like, such as trp promoter (Ptrp), lac promoter (Plac), $P_L$ promoter, $P_R$ promoter, $P_{SE}$ promoter, etc., SPO1 promoter, SPO2 promoter, penP promoter and the like. Also, artificially designed and modified promoters, such as a promoter in which two Ptrp are linked in tandem (Ptrpx2), tac promoter, lacT7 promoter, letI promoter and the like, can be used.

It is preferred to use a plasmid in which the space between Shine-Dalgarno sequence which is the ribosome binding sequence and the initiation codon is adjusted to an appropriate distance (for example, 6 to 18 bases).

The transcription termination sequence is not always necessary for the recombinant DNA of the present invention. However, it is preferred to provide a transcription termination sequence just downstream of the structural gene.

Examples of the procaryote cell include cells of microorganisms belonging to the genus *Escherichia, Serratia, Bacillus, Brevibacterium, Corynebacterium, Microbacterium, Pseudomonas*, or the like. Specific examples include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Serratia ficaria, Serratia fonticola, Serratia liquefaciens, Serratia marcescens, Bacillus subtilis, Bacillus amyloliquefaciens, Brevibacterium immariophilum* ATCC 14068, *Brevibacterium saccharolyticum* ATCC 14066, *Corynebacterium ammoniagenes, Corynebacterium glutamicum* ATCC 13032, *Corynebacterium glutamicum* ATCC 14067, *Corynebacterium glutamicum* ATCC 13869, *Corynebacterium acetoacidophilum* ATCC 13870, *Microbacterium ammoniaphilum* ATCC 15354, *Pseudomonas* sp. D-0110, and the like.

With regard to the method for the introduction of the recombinant DNA, any method for introducing DNA into the above-described host cells, such as the method using calcium ion (*Proc. Natl. Acad. Sci. USA*, 69: 2110 (1972)), the protoplast method(Japanese Published Unexamined Patent Application No. 248394/88), electroporation (*Nucleic Acids Res.*, 16: 6127 (1988)) or the like, can be used.

When yeast is used as the host cell, examples of the expression vector include YEp13 (ATCC 37115), YEp24 (ATCC 37051), YCp50 (ATCC 37419), pHS19, pHS15, and the like.

Any promoter can be used so long as it can function in yeast. Examples include PHO5 promoter, PGK promoter, GAP promoter, ADH promoter, gal 1 promoter, gal 10 promoter, a heat shock polypeptide promoter, MFα1 promoter, CUP 1 promoter and the like.

Examples of the host cell include yeast strains belonging to the genus *Saccharomyces, Schizosaccharomyces, Kluyveromyces, Trichosporon, Schwanniomyces, Pichia, Candida* or the like. Specific examples include *Saccharomyces cerevisiae, Schizosaccharomyces pombe, Kluyveromyces lactis, Trichosporon pullulans, Schwanniomyces alluvius, Pichia pastoris, Candida utilis* and the like.

With regard to the method for the introduction of the recombinant DNA, any method for introducing DNA into yeast, such as electroporation (*Methods in Enzymol.*, 194: 182 (1990)), the spheroplast method (*Proc. Natl. Acad. Sci. USA*, 75: 1929 (1978)), the lithium acetate method (*J. Bacteriol.*, 153: 163 (1983)) and the like, can be used.

When an animal cell is used as the host cell, examples of the expression vector include pcDNAI and pcDM8 (available from Funakoshi), pAGE107 (Japanese Published Unexamined Patent Application No. 22979/91), pAS3-3 (Japanese Published Unexamined Patent Application No. 227075/90), pCDM8 (*Nature*, 329: 840 (1987)), pcDNAI/Amp (manufactured by Invitrogen), pREP4 (manufactured by Invitrogen), pAGE103 (*J. Biochem.*, 101: 1307 (1987)), pAGE210, pAMo, pAMoA and the like.

Any promoter can be used so long as it can function in an animal cell. Examples include a promoter of IE (immediate early) gene of cytomegalovirus (CMV), an early promoter of SV40, a metallothionein promoter, a promoter of retrovirus, a heat shock promoter, SRα promoter, and the like. Also, the enhancer of the IE gene of human CMV can be used together with the promoter.

Examples of the host cell include mouse myeloma cell, rat myeloma cell, mouse hybridoma cell, human Namalwa cell, human Namalwa KJM-1 cell, human fetal kidney cell, human leukemia cell, African grivet kidney cell, Chinese hamster ovary (CHO) cell, HBT5637 (Japanese Published Unexamined Patent Application No. 299/88) and the like.

Examples of the mouse myeloma cell include SP2/0, NSO and the like. Examples of the rat myeloma cell include YB2/0 and the like. Examples of the human fetal kidney cell include HEK293 (ATCC: CRL-1573), and the like. Examples of the human leukemia cell include BALL-1 and the like. Examples of the African grivet kidney cell include COS-1, COS-7 and the like.

The method for introduction of the recombinant DNA into an animal cell is not particularly limited, so long as it is a known method for introducing DNA into an animal cell, such as electroporation (*Cytotechnology*, 3: 133 (1990)), the calcium phosphate method (Japanese Published Unexamined Patent Application No. 227075/90), the lipofection method (*Proc. Natl. Acad. Sci. USA*, 84, 7413 (1987)), the method described in *Virology*, 52: 456 (1973) and the like.

When an insect cell is used as the host cell, the protein can be expressed by the known methods described in, for example, *Baculovirus Expression Vectors, A Laboratory Manual*, W. H. Freeman and Company, New York (1992), *Molecular Biology, A Laboratory Manual, Current Protocols in Molecular Biology, Bio/Technology*, 6: 47 (1988) or the like.

Specifically, a recombinant transfer vector and baculovirus are co-transfected into an insect cell to obtain a recombinant virus in a supernatant of the insect cell culture, and then an insect cell is infected with the resulting recombinant virus to express the protein.

Examples of the transfer vector used in the method include pVL1392, pVL1393 and pBlueBacIII (all manufactured by Invitrogen), and the like.

Examples of the baculovirus include *Autographa californica* nuclear polyhedrosis virus which infects insects of the family *Barathra* and the like.

Examples of the insect cell include *Spodoptera frugiperda* ovary cell, *Trichoplusia ni* ovary cell, *Bombyx mori* ovary-derived culturing cell and the like.

Examples of *Spodoptera frugiperda* ovary cell include Sf9 and Sf21 (*Baculovirus Expression Vectors, A Laboratory Manual*) and the like. Examples of *Trichoplusia ni* ovary cell include High 5 and BTI-TN-5Bl-4 (manufactured by Invitrogen) and the like. Examples of the cell lines derived from silkworm ovary cell include *Bombyx mori* N4 and the like.

The method for co-transfecting the above recombinant transfer vector and the above baculovirus for the preparation of the recombinant virus include the calcium phosphate method (Japanese Published Unexamined Patent Application No. 227075/90), the lipofection method (*Proc. Natl. Acad. Sci. USA*, 84: 7413 (1987)), and the like.

When a plant cell is used as the host cell, examples of expression vector include Ti plasmid, a tobacco mosaic virus vector, and the like.

Any promoter can be used so long as it can function in a plant cell. Examples include 35S promoter of cauliflower mosaic virus (CaMV), rice actin 1 promoter, and the like.

Examples of the host cell include plant cells and the like, such as tobacco, potato, tomato, carrot, soybean, rape, alfalfa, rice, wheat, barley and the like.

The method for introducing the recombinant vector is not particularly limited, so long as it is the general method for introducing DNA into a plant cell, such as the *Agrobacterium* method (Japanese Published Unexamined Patent Application No. 140885/84, Japanese Published Unexamined Patent Application No. 70080/85, WO 94/00977), electroporation (Japanese Published Unexamined Patent Application No. 251887/85), the particle gun method (Japanese Patents 2606856 and 2517813), and the like.

The gene can be expressed as a secretary or fusion protein and the like in accordance with the methods described in *Molecular Cloning*, 2nd ed., in addition to direct expression.

When expressed in yeast, an animal cell or an insect cell, a glycosylated protein can be obtained.

The protein of the present invention can be produced by culturing the thus obtained transformant in a medium to produce and accumulate the protein in the culture, and recovering the protein from the culture.

Culturing of the transformant of the present invention in a medium is carried out according to the conventional method as used in culturing the host of the transformant.

As the medium for culturing the transformant obtained by using, as the host, prokaryote (such as *Escherichia coli* or the like) or eukaryote (such as yeast or the like), the medium may be either a natural medium or a synthetic medium, so long as it is a medium suitable for efficient culturing of the transformant which contains a carbon source, a nitrogen source, an inorganic salt and the like which can be assimilated by the host used.

Examples of the carbon source include those which can be assimilated by the transformant, such as carbohydrates, such as glucose, fructose, sucrose, molasses containing them, starch, starch hydrolysate, etc.; organic acids, such as acetic acid, propionic acid, etc.; alcohols, such as ethanol, propanol, etc.; and the like.

Examples of the nitrogen source include ammonia; various ammonium salts of inorganic acids or organic acids, such as ammonium chloride, ammonium sulfate, ammonium acetate, ammonium phosphate, etc.; other nitrogen-containing compounds; as well as peptone, meat extract, yeast extract, corn steep liquor, casein hydrolysate, soybean meal and soybean meal hydrolysate, various fermented cells and hydrolysates thereof, and the like.

Examples of the inorganic salt include potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

Culturing is usually carried out under aerobic conditions by shaking culture, submerged spinner culture under airation or the like. The culturing temperature is preferably from 15 to 40° C., and the culturing time is generally from 5 hours to 7 days. The pH of the medium is preferably maintained at 3.0 to 9.0 during culturing. The pH can be adjusted using an inorganic or organic acid, an alkali solution, urea, calcium carbonate, ammonia, or the like.

Also, if necessary, antibiotics, such as ampicillin, tetracycline, and the like, can be added to the medium during culturing.

When a microorganism transformed with an expression vector containing an inducible promoter is cultured, an inducer can be added to the medium, if necessary. For example, isopropyl-β-D-thiogalactopyranoside or the like can be added to the medium when a microorganism transformed with an expression vector containing lac promoter is cultured, or indoleacrylic acid or the like can be added thereto when a microorganism transformed with an expression vector containing trp promoter is cultured.

The medium for culturing a transformant obtained using an animal cell as the host includes generally-used media such as RPMI 1640 medium (*The Journal of the American Medical Association*, 199: 519 (1967)), Eagle's MEM (*Science*, 122: 501 (1952)), DMEM (*Virology*, 8: 396 (1959)), and 199 Medium (*Proceeding of the Society for the Biological Medicine*, 73: 1 (1950)), as well as other media to which fetal calf serum or the like has been added to the above media and the like.

Culturing is generally carried out under conditions at pH of 6 to 8 and at 25 to 40° C. for 1 to 7 days in the presence of 5% $CO_2$ or the like.

Furthermore, if necessary, antibiotics, such as kanamycin, penicillin, streptomycin and the like, can be added to the medium during culturing.

The medium for culturing a transformant obtained using an insect cell as the host includes generally-used media such as TNM-FH medium (manufactured by Pharmingen), Sf-900 II SFM (manufactured by Life Technologies), ExCell 400 and ExCell 405 (both manufactured by JRH Biosciences), Grace's Insect Medium (*Nature*, 195: 788 (1962)) and the like.

Culturing is generally carried out under conditions at a pH of 6 to 7 and at 25 to 30° C. for 1 to 5 days or the like.

Furthermore, if necessary, antibiotics, such as gentamicin and the like, can be added to the medium during culturing.

A transformant prepared by using a plant cell as the host cell can be cultured as the cell or after differentiating into a plant cell or organ. Examples of the medium used in culturing of the transformant include Murashige and Skoog (MS) medium, White medium, media to which a plant hormone, such as auxin, cytokinine, or the like has been added, and the like.

Culturing is carried out generally at a pH of 5 to 9 and at 20 to 40° C. for 3 to 60 days.

Also, if necessary, antibiotics, such as kanamycin, hygromycin and the like can be added to the medium during the culturing.

As described above, the protein can be produced by culturing a transformant derived from a microorganism, animal cell or plant cell containing a recombinant vector in which a DNA encoding the protein of the present invention has been inserted according to the general culturing method to produce and accumulate the protein, and recovering the protein from the culture.

The protein of the present invention may be produced by intracellular expression in a host cell, extracellular secretion by a host cell, or production on an outer membrane of the cell. The production method can be selected depending on the kind of the host cell employed or on alternation of the structure of the protein produced.

When the protein of the present invention is produced in a host cell or an outer membrane of the host cell, the protein can be positively secreted extracellularly according to, for example, the method of Paulson et al. (*J. Biol. Chem.*, 264: 17619 (1989)), the method of Lowe et al. (*Proc. Natl. Acad. Sci. USA*, 86: 8227 (1989), *Genes Develop.*, 4: 1288 (1990)), or the methods described in Japanese Published Unexamined Patent Application Nos. 336963/93, WO 94/23021 and the like.

Specifically, the protein of the present invention can actively be secreted extracellularly by expressing it in the form that a signal peptide has been added to the side of N-terminal of a protein containing an active site of the protein of the present invention according to the recombinant DNA technique.

Furthermore, the amount produced can be increased using a gene amplification system, such as by use of a dihydrofolate reductase gene or the like according to the method described in Japanese Published Unexamined Patent Application No. 227075/90.

Moreover, the protein of the present invention can be produced by a transgenic animal individual (transgenic nonhuman animal) or transgenic plant individual (transgenic plant).

When the transformant is the nonhuman animal individual or the plant individual, the protein of the present invention can be produced by breeding or cultivating it so as to produce and accumulate the protein, and recovering the protein from the nonhuman animal individual or the plant individual in a conventional manner.

Examples of the method for producing the protein of the present invention using the nonhuman animal individual include a method for producing the protein of the present invention in a nonhuman animal developed by introducing a gene according to known methods (*American Journal of Clinical Nutrition*, 63: 639S (1996), *American Journal of Clinical Nutrition*, 63: 627S (1996), *Bio/Technology*, 9: 830 (1991)).

In the nonhuman animal individual, the protein can be produced by breeding a transgenic nonhuman animal to which a DNA encoding the protein of the present invention has been introduced to produce and accumulate the protein in the nonhuman animal, and recovering the protein from the nonhuman animal. Examples of the place where production and accumulation of the protein occur in the animal include milk (Japanese Published Unexamined Patent Application No. 309192/88), egg and the like of the animal. Any promoter can be used, so long as it can function in the animal. Suitable examples include an α-casein promoter, a β-casein promoter, a β-lactoglobulin promoter, a whey acidic protein promoter, and the like, which are specific for mammary glandular cells.

As the method for producing the protein of the present invention using the plant individual, mention may be made of the method for producing the protein of the present invention by cultivating a transgenic plant to which the DNA encoding the protein of the present invention has been introduced by a known method (*Tissue Culture*, 20 (1994), *Tissue Culture*, 21 (1994), *Trends in Biotechnol.*, 15: 45 (1997)) to produce and accumulate the protein in the plant, and recovering the protein from the plant in a conventional manner.

The protein produced by the transformant of the present invention can be isolated and purified using the general method for isolating and purifying an enzyme.

For example, when the protein of the present invention is expressed as a soluble product in the host cells, the cells are collected by centrifugation after culturing, suspended in an aqueous buffer, and disrupted using an ultrasonicator, a French press, a Manton Gaulin homogenizer, a Dynomill, or the like to obtain a cell-free extract.

From the supernatant obtained by centrifuging the cell-free extract, a purified product can be obtained by the general method used for isolating and purifying an enzyme, for example, solvent extraction, salting-out using ammonium sulfate or the like, desalting, precipitation using an organic solvent, anion exchange chromatography using a resin, such as diethylaminoethyl (DEAE)-Sepharose, DIAION HPA-75 (manufactured by Mitsubishi Chemical) or the like, cation exchange chromatography using a resin, such as S-Sepharose FF (manufactured by Pharmacia) or the like, hydrophobic chromatography using a resin, such as butyl sepharose, phenyl sepharose or the like, gel filtration using a molecular sieve, affinity chromatography, chromatofocusing, or electrophoresis, such as isoelectronic focusing or the like, alone or in combination thereof.

When the protein is expressed as an inclusion body in the host cells, the cells are collected in the same manner, disrupted and centrifuged to recover the inclusion body of the protein as the precipitate fraction. Next, the inclusion body of the protein is solubilized with a protein-denaturing agent.

The solubilized protein solution is diluted with or dialyzed against a solution containing no protein-denaturing agent or such a dilute solution containing the protein-denaturing agent at a lower concentration that denaturation of the protein is not caused. Thus, the normal tertiary structure of the protein is reconstituted. After the procedure, a purified product of the protein can be obtained by a purification and isolation method similar to the above.

When the protein of the present invention or its glycosylated-derivative is secreted out of cells, the protein or its derivative can be collected from the culture supernatant.

Namely, the culture supernatant is obtained by treating the culture in a similar manner to the above-mentioned centrifugation or the like. Then, a purified product can be obtained from the supernatant using a purification and isolation method similar to the above.

Examples of the thus obtained protein include a protein comprising the amino acid sequence represented by SEQ ID NO:1.

Furthermore, a fusion protein of the protein of the present invention and other protein may be produced, and purified by affinity chromatography using a substance having affinity to the fusion protein. For example, the protein of the present invention may be produced as a fusion protein with protein A according to the method of Lowe et al. (*Proc. Natl. Acad. Sci. USA*, 86: 8227 (1989); *Genes Develop.*, 4: 1288 (1990)), or the method described in Japanese Published Unexamined Patent Application No. 336963/93 or WO 94/23021, and purified by affinity chromatography using immunoglobulin G.

Moreover, the protein of the present invention may be produced as a fusion protein with Flag peptide, and the fusion protein can be purified by affinity chromatography using an anti-Flag antibody (*Proc. Natl. Acad. Sci., USA*, 86: 8227 (1989), *Genes Develop.*, 4: 1288 (1990)). Further purification can be carried out by affinity chromatography using the antibody against the protein per se.

Also, based on the information of the thus obtained protein, the protein of the present invention can be produced by the chemical synthesis method, such as Fmoc (fluorenylmethyloxycarbonyl) method, tBoc (t-butyloxycarbonyl) method, or the like. It can also be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

<3> Preparation of N-Acetylmannosamine

N-Acetylmannosamine can be produced in an aqueous medium using a culture of the transformant obtained by the culturing described in (2) or a treated product of the culture as the enzyme source.

Examples of the treated product of the culture include a concentrate of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells, an enzyme preparation obtained by extraction from the cell, and the like.

The enzyme source for use in the production of N-acetylmannosamine is used in a concentration of 1 mU/l to 1,000 U/l, preferably 10 mU/l to 100 U/l, when the activity capable of producing 1 $\mu$mol of N-acetylmannosamine at 37° C. in 1 minute is defined as 1 unit (U).

Examples of the aqueous medium for use in the production of N-acetylmannosamine include water; buffer solutions of phosphate, carbonate, acetate, borate, citrate, tris, etc.; alcohols such as methanol, ethanol, etc.; esters, such as ethyl acetate, etc.; ketones, such as acetone, etc.; amides, such as acetamide, etc.; and the like. Also, the microbial culture which have been used as the enzyme source can be used as an aqueous medium.

In the production of N-acetylmannosamine, a surfactant or an organic solvent may be added, if necessary. Any surfactant capable of accelerating the production of N-acetylmannosamine may be used as the surfactant. Examples include nonionic surfactants, such as polyoxyethylene octadecylamine (e.g., Nymeen S-215, manufactured by Nippon Oil & Fats), etc.; cationic surfactants, such as cetyltrimethylammonium bromide, alkyldimethyl benzylammoniumchloride (e.g., Cation F2-40E, manufactured by Nippon Oil & Fats), etc.; anionic surfactants, such as lauroyl sarcosinate, etc.; tertiary amines, such as alkyldimethylamine (e.g., Tertiary Amine FB, manufactured by Nippon Oil & Fats), etc.; and the like, which are used alone or as a mixture of two or more. The surfactant is used generally in a concentration of 0.1 to 50 g/l. Examples of the organic solvent include xylene, toluene, fatty acid alcohol, acetone, ethyl acetate, and the like, which are used in a concentration of generally 0.1 to 50 ml/l.

The production reaction of N-acetylmannosamine is carried out in an aqueous medium having a pH of 5 to 10, preferably 6 to 8, at 20 to 50° C. for 1 to 96 hours. In this production reaction, ATP, inorganic salts such as $MgCl_2$ etc., and the like can be added, if necessary.

The amount of N-acetylmannosamine produced in the aqueous medium can be determined, for example, using a glycosyl-analyzer manufactured by Dionex (*Anal. Biochem.*, 189: 151 (1990)).

The N-acetylmannosamine produced in the aqueous medium can be collected by the ordinary methods using activated carbon, ion exchange resins, and the like.

Figure 1:
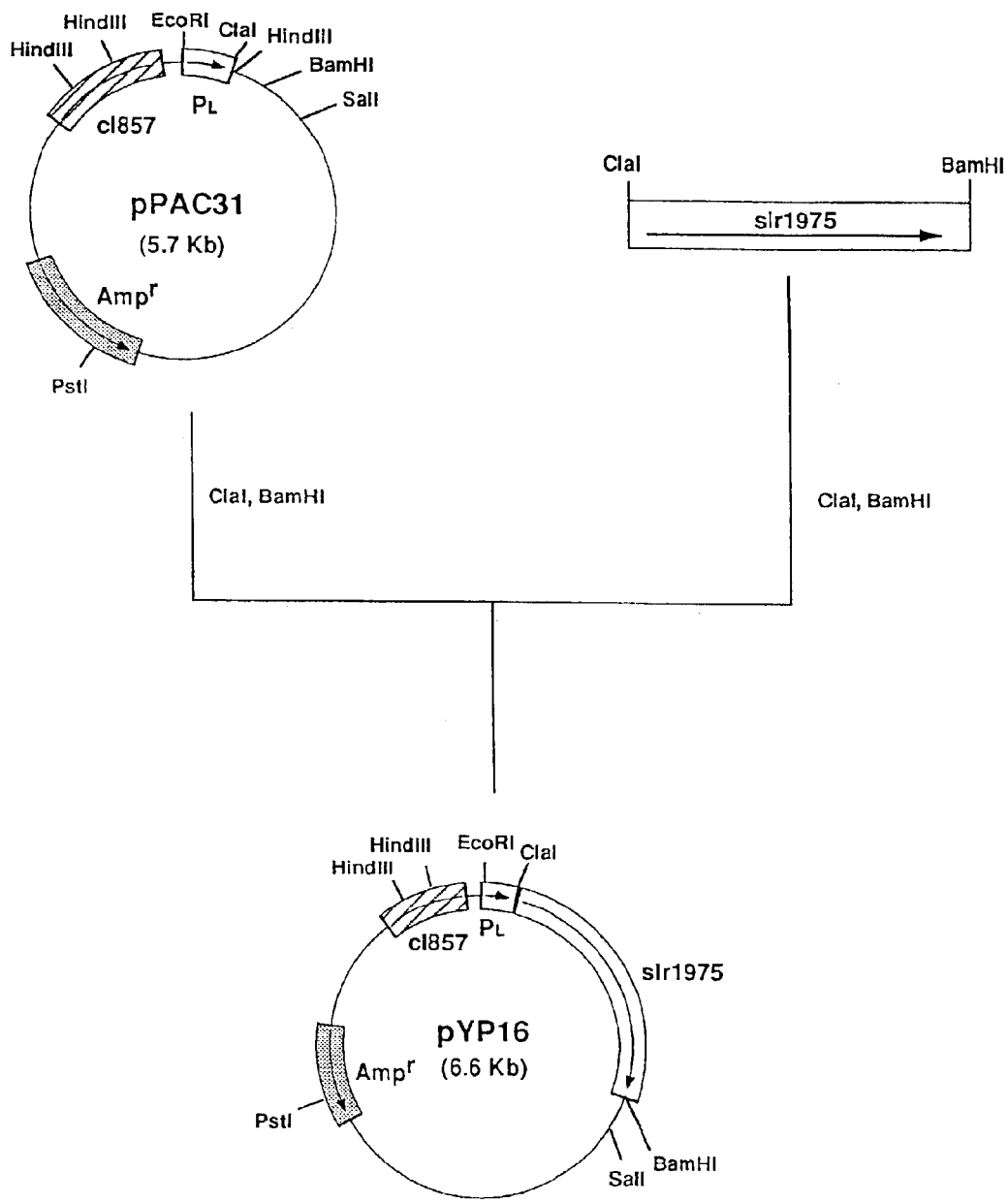
FIG. 1 shows construction steps of N-acetylglucosamine 2-epimerase expression plasmid pYP16.

Amp$^r$: ampicillin resistant gene $P_L$: $P_L$ promoter cI857: cI857 repressor slr1975: N-acetylglucosamine 2-epimerase gene

BEST MODE FOR CARRYING OUT THE INVENTION

Examples of the present invention are illustrated below, but the present invention is not limited thereto.

EXAMPLE 1

Homology Search on Data Base

A similarity search was carried out in Blast Search of Genbank and CyanoBase (http://www.kazusa.or.jp/cyano/) as the data base of *Synechocystis* sp. (PCC 6803) genomic DNA sequence using the amino acid sequence of swine N-acetylglucosamine 2-epimerase (*J. Biol. Chem.*, 271: 16294 (1996)) as the Query.

As a result, it was revealed that this amino acid sequence has a high homology with a sequence (slr1975) derived from *Synechocystis* sp. (PCC 6803), which is described as a renin-binding protein having the amino acid sequence represented by SEQ ID NO:1 and encoded by the DNA having the nucleotide sequence represented by SEQ ID NO:2.

EXAMPLE 2

Construction of a Strain Expressing a Gene Derived from *Synechocystis*:

*Synechocystis* sp. (PCC 6803) was cultured by a method described in *J. Gen. Microbiol.*, 111: 1 (1979).

After culturing, chromosomal DNA of the microorganism was isolated and purified by the method described in *Current Protocols in Molecular Biology*.

A DNA fragment containing the gene selected in Example 1 was amplified by the following method using the DNAs of SEQ ID NO:3 and 4 synthesized using DNA Synthesizer 8905 Type manufactured by Perceptive Biosystems.

PCR was carried out using the above synthesized DNAs as primers and the *Synechocystis* sp. (PCC 6803) chromosomal DNA as the template. Using 40 $\mu$l of a reaction solution containing 0.1 $\mu$g of the chromosomal DNA, 0.5 $\mu$mol/l each primer, 2.5 units of Pfu DNA polymerase (manufactured by STRATAGENE), 4 $\mu$l of a 10-fold concentrated buffer solution for Pfu DNA polymerase use (manufactured by STRATAGENE) and 200 $\mu$mol/l each deoxy NTP, PCR was carried out by 30 cycles, one cycle consisting of reaction at 94° C. for 1 minute, reaction at 42° C. for 2 minutes and reaction at 72° C. for 3 minutes.

Amplification of the desired fragment was confirmed by subjecting one-tenth volume of the reaction solution to agarose gel electrophoresis, and then the remaining reaction solution was mixed with the same volume of TE (10 mmol/l Tris-HCl (pH 8.0), 1 mmol/l EDTA) saturated phenol/chloroform (1 vol/1 vol).

After the mixed solution was centrifuged, the thus obtained upper layer was mixed with 2 volumes of cold ethanol and the mixture was allowed to stand at −80° C. for 30 minutes. The resulting solution was centrifuged to obtain the DNA precipitate.

The DNA precipitate was dissolved in 20 µl of TE.

Using 5 µl of the dissolved solution, the DNA was digested with restriction enzymes ClaI and BamHI, DNA fragments were separated using agarose gel electrophoresis and then a DNA fragment of 1.0 kb was recovered using GeneClean II Kit.

After 0.2 µg of pPAC31 (WO 98/12343) DNA was digested with restriction enzymes ClaI and BamHI, DNA fragments were separated using agarose gel electrophoresis to recover a DNA fragment of 5.5 kb in the same manner.

Using a ligation kit, the 1.0 kb and 5.5 kb fragments were subjected to the ligation reaction at 16° C. for 16 hours.

Using the ligation reaction solution, *Escherichia coli* NM522 was transformed in accordance with the known method, and the transformants were spread onto LB agar medium containing 50 µg/ml ampicillin, followed by culturing overnight at 30° C.

A plasmid was extracted from the thus grown transformant colonies in accordance with the known method to obtain expression plasmid pYP16. Structure of this plasmid was confirmed by restriction enzyme digestion (FIG. 1).

EXAMPLE 3

Production of N-Acetylglucosamine:

*Escherichia coli* NM522/pYP16 obtained in Example 2 was inoculated into a large test tube charged with 8 ml of LB medium containing 50 µg/ml ampicillin, followed by culturing at 28° C. for 17 hours. The culture was inoculated into a large test tube charged with 8 ml of LB medium containing 50 µg/ml ampicillin, with an inoculum size of 1%, followed by culturing at 30° C. for 4 hours and then at 40° C. for 3 hours. The culture was centrifuged to obtain wet cells. According to need, the wet cells could be stored at −20° C. and could be used by thawing prior to use.

The reaction was carried out at 37° C. for 2 hours in 0.1 ml of a reaction solution containing 60 mg/ml the wet cells in final concentration, 100 mmol/l Tris-HCl (pH 7.4), 10 mmol/l $MgCl_2$, 40 mmol/l N-acetylmannosamine, 4 mmol/l ATP and 0.4% Nymeen S-215.

After completion of the reaction, the reaction product was analyzed using a glycosyl-analyzer manufactured by Dionex (DX-500) to confirm that 13.7 mmol/l N-acetylglucosamine was produced and accumulated in the reaction solution.

Production of N-acetylglucosamine was not found in *E. coli* NM522/pPAC31 containing the vector alone.

EXAMPLE 4

Production of N-acetylmannosamine:

*Escherichia Coli* NM522/pYP16 obtained in Example 2 was inoculated into a large test tube charged with 8 ml of LB medium containing 50 µg/ml ampicillin, followed by culturing at 28° C. for 17 hours.

The culture was inoculated into a large test tube charged with 8 ml of LB medium containing 50 µg/ml ampicillin, with an inoculum size of 1%, followed by culturing at 28° C. for 4 hours and then at 40° C. for 3 hours. The culture was centrifuged to obtain wet cells. According to need, the wet cells could be stored at −20° C. and could be used by thawing prior to use.

The reaction was carried out at 37° C. for 2 hours in 0.1 ml of a reaction solution containing 60 mg/ml the wet cells in final concentration, 100 mmol/l Tris-HCl (pH 7.4), 10 mmol/l $MgCl_2$, 500 mmol/l N-acetylglucosamine, 4 mmol/l ATP and 0.4% Nymeen S-215.

After completion of the reaction, the reaction product was analyzed using a glycosyl-analyzer manufactured by Dionex (DX-500) to confirm that 70 mmol/l N-acetylmannosamine was produced and accumulated in the reaction solution.

Production of N-acetylglucosamine was not found in *E. coli* NM522/pPAC31 containing the vector alone.

INDUSTRIAL APPLICABILITY

According to the present invention, a large amount of N-acetylglucosamine 2-epimerase can be produced according to recombination DNA technique. Also, N-acetylmannosamine can efficiently be produced using the enzyme.

| Sequence Listing Free Text | |
|---|---|
| SEQ ID NO:3 | Synthetic DNA |
| SEQ ID NO:4 | Synthetic DNA |

What is claimed is:

1. An isolated or purified DNA consisting of the nucleotide sequence represented by SEQ ID NO:2.

2. A recombinant DNA obtained by inserting the DNA according to claim 1 into a vector.

3. A transformant obtainable by introducing the recombinant DNA according to claim 2 into a host cell.

4. The transformant according to claim 3, wherein the host cell is *Escherichia coli*.

5. A process for producing a protein having N-acetylglucosamine 2-epimerase activity, which comprises culturing a transformant which contains a DNA comprising the nucleotide sequence represented by SEQ ID NO:2 in a medium to produce and accumulate a protein having N-acetylglucosamine 2-epimerase activity in the culture; and recovering the protein from the culture.

6. The process according to claim 5, wherein said transformant is *Escherichia coli*.

7. A process for producing N-acetylmannosamine, which comprises selecting, as an enzyme source, a culture of the transformant which contains a DNA comprising the nucleotide sequence represented by SEQ ID NO:2 or a treated product of the culture which is selected from the group consisting of a concentrate of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells, and an enzyme preparation obtained by extraction from the cell; allowing the enzyme source and N-acetylglucosamine to be present in an aqueous medium to produce and accumulate N-acetylmannosamine in the aqueous medium; and recovering N-acetylmannosamine from the aqueous medium.

8. The process according to claim 7, wherein said transformant is *Escherichia coli*.

9. A process for producing N-acetylmannosamine, which comprises:

selecting, as an enzyme source, a culture of a transformant which contains a DNA hybridizing with a DNA consisting of the nucleotide sequence represented by SEQ ID NO:2 under stringent conditions and encoding a protein having N-acetylglucosamine 2-epimerase activity derived from a microorganism belonging to *Cyanobacteria*, or a treated product of the culture which is selected from the group consisting of a concentrate of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells, and an enzyme preparation obtained by extraction from the cells;

allowing the enzyme source and N-acetylglucosamine to be present in an aqueous medium to produce and accumulate N-acetylmannosamine in the aqueous medium; and recovering N-acetylmannosamine from the aqueous medium.

10. The process for producing N-acetylmannosamine according to claim 9, wherein the microorganism belonging to *Cyanobacteria* is a microorganism belonging to the genus *Synechocystis*.

11. The process for producing N-acetylmannosamine according to claim 9, wherein the DNA encodes the protein represented by SEQ ID NO:1.

* * * * *

SEQUENCE LISTING

<160> NUMBER OF SEQ ID NOS: 4

<210> SEQ ID NO 1
<211> LENGTH: 391
<212> TYPE: PRT
<213> ORGANISM: Synechocystis sp.(PCC6803)

<400> SEQUENCE: 1

Met Ile Ala His Arg Arg Gln Glu Leu Ala Gln Gln Tyr Tyr Gln Ala
 1               5                  10                  15

Leu His Gln Asp Val Leu Pro Phe Trp Glu Lys Tyr Ser Leu Asp Arg
            20                  25                  30

Gln Gly Gly Gly Tyr Phe Thr Cys Leu Asp Arg Lys Gly Gln Val Phe
        35                  40                  45

```
Asp Thr Asp Lys Phe Ile Trp Leu Gln Asn Arg Gln Val Trp Gln Phe
    50                  55                  60
Ala Val Phe Tyr Asn Arg Leu Glu Pro Lys Pro Gln Trp Leu Glu Ile
 65                  70                  75                  80
Ala Arg His Gly Ala Asp Phe Leu Ala Arg His Gly Arg Asp Gln Asp
                 85                  90                  95
Gly Asn Trp Tyr Phe Ala Leu Asp Gln Glu Gly Lys Pro Leu Arg Gln
            100                 105                 110
Pro Tyr Asn Val Phe Ser Asp Cys Phe Ala Ala Met Ala Phe Ser Gln
        115                 120                 125
Tyr Ala Leu Ala Ser Gly Ala Gln Glu Ala Lys Ala Ile Ala Leu Gln
    130                 135                 140
Ala Tyr Asn Asn Val Leu Arg Arg Gln His Asn Pro Lys Gly Gln Tyr
145                 150                 155                 160
Glu Lys Ser Tyr Pro Gly Thr Arg Pro Leu Lys Ser Leu Ala Val Pro
                165                 170                 175
Met Ile Leu Ala Asn Leu Thr Leu Glu Met Glu Trp Leu Leu Pro Pro
            180                 185                 190
Thr Thr Val Glu Glu Val Leu Ala Gln Thr Val Arg Glu Val Met Thr
        195                 200                 205
Asp Phe Leu Asp Pro Glu Ile Gly Leu Met Arg Glu Ala Val Thr Pro
    210                 215                 220
Thr Gly Glu Phe Val Asp Ser Phe Glu Gly Arg Leu Leu Asn Pro Gly
225                 230                 235                 240
His Gly Ile Glu Ala Met Trp Phe Met Met Asp Ile Ala Gln Arg Ser
                245                 250                 255
Gly Asp Arg Gln Leu Gln Glu Gln Ala Ile Ala Val Val Leu Asn Thr
            260                 265                 270
Leu Glu Tyr Ala Trp Asp Glu Glu Phe Gly Gly Ile Phe Tyr Phe Leu
        275                 280                 285
Asp Arg Gln Gly His Pro Pro Gln Gln Leu Glu Trp Asp Gln Lys Leu
    290                 295                 300
Trp Trp Val His Leu Glu Thr Leu Val Ala Leu Ala Lys Gly His Gln
305                 310                 315                 320
Ala Thr Gly Gln Glu Lys Cys Trp Gln Trp Phe Glu Arg Val His Asp
                325                 330                 335
Tyr Ala Trp Ser His Phe Ala Asp Pro Glu Tyr Gly Glu Trp Phe Gly
            340                 345                 350
Tyr Leu Asn Arg Arg Gly Glu Val Leu Leu Asn Leu Lys Gly Gly Lys
        355                 360                 365
Trp Lys Gly Cys Phe His Val Pro Arg Ala Leu Trp Leu Cys Ala Glu
    370                 375                 380
Thr Leu Gln Leu Pro Val Ser
385                 390

<210> SEQ ID NO 2
<211> LENGTH: 1173
<212> TYPE: DNA
<213> ORGANISM: Synechocystis sp.(PCC6803)

<400> SEQUENCE: 2 atg att gcc cat cgc cgt cag gag tta gcc cag caa tat tac cag gct     48
Met Ile Ala His Arg Arg Gln Glu Leu Ala Gln Gln Tyr Tyr Gln Ala
  1               5                  10                  15 tta cac cag gac gta ttg ccc ttt tgg gaa aaa tat tcc ctc gat cgc     96
```

```
                Leu His Gln Asp Val Leu Pro Phe Trp Glu Lys Tyr Ser Leu Asp Arg
                            20                  25                  30 cag ggg ggc ggt tac ttt acc tgc tta gac cgt aaa ggc cag gtt ttt       144
Gln Gly Gly Gly Tyr Phe Thr Cys Leu Asp Arg Lys Gly Gln Val Phe
            35                  40                  45 gac aca gat aaa ttc att tgg tta caa aac cgt cag gta tgg cag ttt       192
Asp Thr Asp Lys Phe Ile Trp Leu Gln Asn Arg Gln Val Trp Gln Phe
 50                  55                  60 gcc gtt ttc tac aac cgt ttg gaa cca aaa ccc caa tgg tta gaa att       240
Ala Val Phe Tyr Asn Arg Leu Glu Pro Lys Pro Gln Trp Leu Glu Ile
 65                  70                  75                  80 gcc cgc cat ggt gct gat ttt tta gct cgc cac ggc cga gat caa gac       288
Ala Arg His Gly Ala Asp Phe Leu Ala Arg His Gly Arg Asp Gln Asp
                85                  90                  95 ggt aat tgg tat ttt gct ttg gat cag gaa ggc aaa ccc ctg cgt caa       336
Gly Asn Trp Tyr Phe Ala Leu Asp Gln Glu Gly Lys Pro Leu Arg Gln
            100                 105                 110 ccc tat aac gtt ttt tcc gat tgc ttc gcc gcc atg gcc ttt agt caa       384
Pro Tyr Asn Val Phe Ser Asp Cys Phe Ala Ala Met Ala Phe Ser Gln
        115                 120                 125 tat gcc tta gcc agt ggg gcg cag gaa gct aaa gcc att gcc ctg cag       432
Tyr Ala Leu Ala Ser Gly Ala Gln Glu Ala Lys Ala Ile Ala Leu Gln
130                 135                 140 gcc tac aat aac gtc cta cgc cgt cag cac aat ccc aaa ggt caa tac       480
Ala Tyr Asn Asn Val Leu Arg Arg Gln His Asn Pro Lys Gly Gln Tyr
145                 150                 155                 160 gag aag tcc tat cca ggt act aga ccc ctc aaa tcc ctg gcg gtg ccg       528
Glu Lys Ser Tyr Pro Gly Thr Arg Pro Leu Lys Ser Leu Ala Val Pro
                165                 170                 175 atg att tta gcc aac ctc acc ctg gag atg gaa tgg tta tta ccg cct       576
Met Ile Leu Ala Asn Leu Thr Leu Glu Met Glu Trp Leu Leu Pro Pro
            180                 185                 190 act acc gtg gaa gag gtg ttg gcc caa acc gtc aga gaa gtg atg acg       624
Thr Thr Val Glu Glu Val Leu Ala Gln Thr Val Arg Glu Val Met Thr
        195                 200                 205 gat ttc ctc gac cca gaa ata gga tta atg cgg gaa gcg gtg acc ccc       672
Asp Phe Leu Asp Pro Glu Ile Gly Leu Met Arg Glu Ala Val Thr Pro
210                 215                 220 aca gga gaa ttt gtt gat agt ttt gaa ggg cgg ttg ctc aac cca gga       720
Thr Gly Glu Phe Val Asp Ser Phe Glu Gly Arg Leu Leu Asn Pro Gly
225                 230                 235                 240 cac ggc att gaa gcc atg tgg ttc atg atg gac att gcc caa cgc tcc       768
His Gly Ile Glu Ala Met Trp Phe Met Met Asp Ile Ala Gln Arg Ser
                245                 250                 255 ggc gat cgc cag tta cag gag caa gcc att gca gtg gtg ttg aac acc       816
Gly Asp Arg Gln Leu Gln Glu Gln Ala Ile Ala Val Val Leu Asn Thr
            260                 265                 270 ctg gaa tat gcc tgg gat gaa gaa ttt ggt ggc ata ttt tat ttc ctt       864
Leu Glu Tyr Ala Trp Asp Glu Glu Phe Gly Gly Ile Phe Tyr Phe Leu
        275                 280                 285 gat cgc cag ggc cac cct ccc caa caa ctg gaa tgg gac caa aag ctc       912
Asp Arg Gln Gly His Pro Pro Gln Gln Leu Glu Trp Asp Gln Lys Leu
290                 295                 300 tgg tgg gta cat ttg gaa acc ctg gtt gcc cta gcc aag ggc cac caa       960
Trp Trp Val His Leu Glu Thr Leu Val Ala Leu Ala Lys Gly His Gln
305                 310                 315                 320 gcc act ggc caa gaa aaa tgt tgg caa tgg ttt gag cgg gtc cat gat      1008
Ala Thr Gly Gln Glu Lys Cys Trp Gln Trp Phe Glu Arg Val His Asp
                325                 330                 335
```

-continued

```
tac gcc tgg agt cat ttc gcc gat cct gag tat ggg gaa tgg ttt ggc      1056
Tyr Ala Trp Ser His Phe Ala Asp Pro Glu Tyr Gly Glu Trp Phe Gly
            340             345             350 tac ctg aat cgc cgg gga gag gtg tta ctc aac cta aaa ggg ggg aaa      1104
Tyr Leu Asn Arg Arg Gly Glu Val Leu Leu Asn Leu Lys Gly Gly Lys
            355             360             365 tgg aaa ggg tgc ttc cac gtg ccc cga gct ctg tgg ctc tgt gcg gaa      1152
Trp Lys Gly Cys Phe His Val Pro Arg Ala Leu Trp Leu Cys Ala Glu
    370             375             380 act ctc caa ctt ccg gtt agt                                          1173
Thr Leu Gln Leu Pro Val Ser
385             390

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence :Synthetic
      DNA

<400> SEQUENCE: 3
taaatcgata tttgtatgat tgcccatcgc cgtcag                                36

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence :Synthetic
      DNA

<400> SEQUENCE: 4
aaaggatcct taactaaccg gaagttggag agtttc                                36
```